United States Patent [19]

Fujii et al.

[11] Patent Number: 4,503,045
[45] Date of Patent: Mar. 5, 1985

[54] 2'-DEOXY-3',5'-DI-O-ALKYLCARBONYL-5-FLUOROURIDINE DERIVATIVES, A PROCESS FOR THE PREPARATION OF THE DERIVATIVES AND ANTI-TUMOR AGENTS CONTAINING THE DERIVATIVES

[75] Inventors: Setsuro Fujii, Osaka; Bompei Yasui, Nara; Tomohisa Miyamoto, Osaka; Masatoshi Shiga, Osaka; Kazuko Ando, Osaka; Iwao Hashimoto, Osaka; Masahiro Kawasaki, Nara; Yoichiro Kawai; Yuji Mino, both of Osaka, all of Japan

[73] Assignee: Funai Yakuhin Kogyo Kabushiki Kaisha, Osaka, Japan

[21] Appl. No.: 234,569

[22] Filed: Feb. 13, 1981

[30] Foreign Application Priority Data

Feb. 15, 1980 [JP] Japan .................. 55-17408

[51] Int. Cl.³ .................. A61K 31/70; C07H 19/08
[52] U.S. Cl. .................. 514/25; 536/23; 514/50
[58] Field of Search .................. 586/23; 424/180

[56] References Cited

U.S. PATENT DOCUMENTS 3,853,845 12/1974 Rousseau et al. .................. 536/23

FOREIGN PATENT DOCUMENTS 2025401 1/1980 United Kingdom .

OTHER PUBLICATIONS

Carter et al., *New Drugs in Cancer Chemotherapy*, pp. 1-2, (1981).
Halnan, *Treatment of Cancer*, p. 80, (1982).
Hoshi et al., *Farumashia*, vol. 9, No. 7, pp. 464-468, (1973), and English translation of pertinent portions.
Oslo, *Remington's Pharmaceutical Sciences*, 16th Ed., pp. 1081-1082, Chapter 62, (1980).
Nodine et al., *Animal and Clinical, Pharmacologic Techniques in Drug Evaluation*, p. 632, (1964).
Dukes, *Side Effects of Drugs Annual I*, p. 336, (1977).
Holland et al., *Cancer Medicine*, pp. 675-675, (1973).
Laurence et al., *Evaluation of Drug Activities: Pharmacometrics*, vol. 2, p. 842, (1964).
Siegler et al., *Animal and Clinical, Pharmacologic Techniques in Drug Evaluation*, vol. 2, pp. 830, 834, (1967).
Oslo et al., *The United States Dispensatory*, 27th Ed., pp. 377-378, 527-528, (1973).
Baker et al., *Physicians' Desk Reference*, 32nd Ed., p. 1387, (1978).
Grollman et al., *Pharmacology and Therapeutics*, pp. 669-670, (1970).

*Primary Examiner*—Blondel Hazel
*Attorney, Agent, or Firm*—Birch, Stewart, Kolasch & Birch

[57] ABSTRACT

2'-Deoxy-3',5'-di-O-alkylcarbonyl-5-fluorouridine derivatives possessing strong anti-tumor activity with weak toxicity and represented by the general formula:

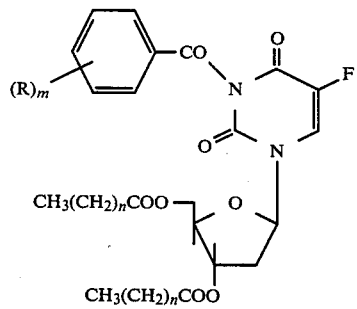

wherein R stands for an alkyl group, an alkoxy group or a halogen atom, m for zero or an integer of 1-3, and n for an integer of 1-14, with the proviso that when m is 2 or 3, R's may be the same or different and that when m is 2 and the adjacent two R's are alkoxy groups, the two alkyl moieties of the alkoxy groups may be combined to form together with the two adjacent oxa bridging members an alkylenedioxy group as a whole. These derivatives are prepared by acylating a 2'-deoxy-3',5'-di-O-alkylcarbonyl-5-fluorouridine with corresponding benzoyl halides and are useful as active ingredients for anti-tumor agents, especially for oral administration.

31 Claims, No Drawings

2'-DEOXY-3',5'-DI-O-ALKYLCARBONYL-5-FLUOROURIDINE DERIVATIVES, A PROCESS FOR THE PREPARATION OF THE DERIVATIVES AND ANTI-TUMOR AGENTS CONTAINING THE DERIVATIVES

BACKGROUND AND FIELD OF THE INVENTION

The present invention relates to 2'-Deoxy-3',5'-di-O-alkylcarbonyl-5-fluorouridine derivatives, a process for the preparation of the derivatives and anti-tumor agents containing the derivatives as active ingredients thereof. More particularly, the present invention relates to new 2'-deoxy-3',5'-di-O-alkylcarbonyl-5-fluorouridine derivatives of the general formula:

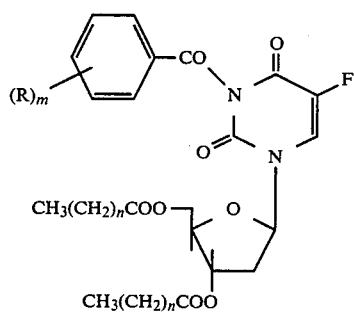

wherein R stands for an alkyl group, an alkoxy group or a halogen atom, m for zero or an integer of 1–3, and n for an integer of 1–14, with the proviso that when m is 2 or 3, R's may be the same or different and that when m is 2 and the adjacent two R's are alkoxy groups, the two alkyl moieties of the alkoxy groups may be combined to form together with the two adjacent oxa bridging members an alkylenedioxy group as a whole, a process for the preparation of the derivatives wherein a 2'-deoxy-3',5'-di-O-alkylcarbonyl-5-fluorouridine is reacted with a benzoyl halide derivative, and anti-tumor agents containing the 2'-deoxy-3',5'-di-O-alkylcarbonyl-5-fluorouridine derivatives as active ingredients thereof.

In the field of chemotherapy, the major public attention is now directed to the development of effective anti-tumor agents. Heretofore, various kinds of 5-fluorouridine derivatives have been developed as anti-tumor agents. However, all of these derivatives are quite unsatisfactory as they are either poor in the inherent anti-tumor activity or exhibit strong toxicity. 2'-Deoxy-5-fluorouridine (referred to hereinafter simply as FUDR) is already used as an anti-tumor agent but this compound is exceptionally high in toxicity for medication and has a narrower safety region. In addition, this compound is subject to a considerable limitations in actual therapeutic applications since the mode of administering this compound is limited only to intraarterial injection, or in other words, this compound cannot be administered orally [Physicians' Desk Reference, p. 1387 (1978)].

Heretofore, extensive researches have been made by C. Heidelberger et al. on the mechanism of anti-tumor activity of FUDR and a variety of studies have also been made by them to develop new FUDR derivatives which are devoid of such drawbacks and possess a high level of anti-tumor activity of chemical modification of FUDR. As a result of the studies 2'-deoxy-3',5'-di-O-acetyl-5-fluorouridine (referred to hereinafter simply as acetyl-FUDR) as one of the new chemically modified FUDR derivatives was found to possess such a property that this compound is hardly decomposed in living body, thus suggesting the possibility of oral administration [Cancer Research, 23, 49 et seq. (1963)]. As a result of experiments made on anti-tumor activity of the acetyl-FUDR, however, this compound is evaluated to be almost equivalent in anti-tumor activity to FUDR or rather poor in effectiveness [Biochem. Pharmacology, 14, 1605 et seq., (1965); Cancer Research, 23, 420 et seq. (1963)]. Thus, the acetyl-FUDR is still unsatisfactory as a practically effective anti-tumor agent.

A number of researches have thus been made on FUDR derivatives and results of the researches are summarized, for example, as a correlation between the chemical structure and the anti-tumor activity of FUDR and its derivatives in Cancer Research, 30, 1555–6 (1970).

In this reference, three enzymatic activities which were found to keys to the development of anti-tumor activity as a result of clarifying the mechanism of anti-tumor activity exhibited by FUDR are taken up as subjects and an explanatory diagram is given to show that positions and what structures of the FUDR molecule are necessary for exhibiting anti-tumor activity. In this reference, however, it is stated that the nitrogen atom in 3-position of the uracil (pyrimidine or pyrimidione) ring of FUDR should not be substituted.

3',5'-Dialkyl esters of FUDR are also reported as derivatives of FUDR but they are still unsatisfactory with respect to anti-tumor activity and toxicity [Biochem. Pharmacology, 14. 1605–1619 (1965), ibid. 15, 627–644 (1966)]. Recently, FUDR and acetyl-FUDR derivatives have been reported wherein the hydrogen atom bonded to the 3-nitrogen atom on the uracil ring is substituted by a specific aroyl group (UK Patent Appln. No. 2,025,401 published on Jan. 23, 1980 and European Patent Appln. No. 9,882 published on Apr. 16, 1980). However, further enhancement in anti-tumor activity is desired also in these compounds. Thus, there is a great demand for developing new FUDR derivatives which possess strong anti-tumor activity with weak toxicity and are suited for oral administration without the necessity of troublesome intraarterial or intravenous injection.

OBJECTS OF THE INVENTION

Accordingly, it is an object of the present invention to provide new 2'-deoxy-3',5'-di-O-alkylcarbonyl-5-fluorouridine derivatives of the general formula (I) possessing strong anti-tumor activity with a low level of toxicity.

It is another object of the present invention to provide a process for the preparation of the new 2'-deoxy-3',5'-di-O-alkylcarbonyl-5-fluorouridine derivatives of the general formula (I).

It is further object of the present invention to provide the use of the new 2'-deoxy-3',5'-di-O-alkylcarbonyl-5-fluorouridine derivatives of the general formula (I) as anti-tumor agents.

It is still another object of the present invention to provide anti-tumor agents containing the new compounds of the general formula (I) as active ingredient.

It is still further object of the present invention to provide anti-tumor agents useful for both injection and oral administration.

It is yet further object of the present invention to provide the use of the anti-tumor agents for chemotherapy of tumors.

Other objects, features and advantages of the present invention will become more fully apparent from the following description.

DETAILED DESCRIPTION OF THE INVENTION

With a view to developing new 2'-deoxy-3',5'-di-O-alkylcarbonyl-5-fluorouridine derivatives possessing a high level of anti-tumor activity with weak toxicity, the present inventors have made extensive researches on new classes of 2'-deoxy-3',5'-di-O-alkylcarbonyl-5-fluorouridine derivatives prepared from various 2'-deoxy-3',5'-di-O-alkylcarbonyl-5-fluorouridines.

As a result of the extensive researches, it has now surprisingly been found that the new compounds of the general formula (I) are superior in anti-tumor activity to the known similar compounds at an equivalent toxicity level. The present invention has been accomplished on the basis of the above finding.

In accordance with one embodiment of the present invention, there are provided new 2'-deoxy-3',5'-di-O-alkylcarbonyl-5-fluorouridine derivatives of the general formula:

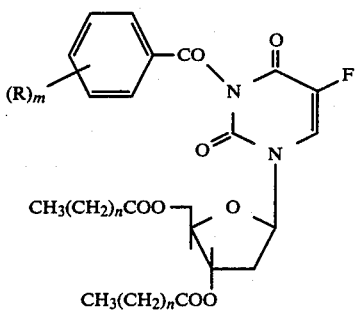

(I)

wherein R stands for an alkyl group, an alkoxy group or a halogen atom, m for zero or an integer of 1–3, and n for an integer of 1–14, with the proviso that when m is 2 or 3, R's may be the same or different and that when m is 2 and the adjacent two R's are alkoxy groups, the two alkyl moieties of the alkoxy groups may be combined to form together with the two adjacent oxa bridging members an alkylenedioxy group as a whole.

In the general formula (I), the benzoyl group introduced into 3-position of the uracil ring may be ring-substituted with up to 3(R) radicals which may be the same or different and each represent an alkyl group, an alkoxy group or a halogen atom. When R stands for an alkyl group, straight or branched chain $C_{1-20}$ alkyl groups are possible, such as methyl, ethyl, n-propyl, isopropyl, n-butyl, sec-butyl, tert-butyl, n-pentyl, isopentyl, n-hexyl, n-octyl, n-decyl, n-dodecyl, n-hexadecyl and n-octadecyl. Illustrative of substituents wherein R is an alkoxy group are, for example, straight or branched chain $C_{1-20}$ alkoxy groups such as methoxy, ethoxy, n-propoxy, isopropoxy, n-butoxy, isobutoxy, sec-butoxy, tert-butoxy, n-pentyloxy, n-hexyloxy, n-octyloxy, n-decyloxy, n-dodecyloxy, n-hexadecyloxy and n-octadecyloxy groups.

When two vicinal lower alkoxy groups exist as ring-substituents in the benzoyl group (R=a lower alkoxy group and m=2), the alkyl moieties of the two lower alkoxy groups may be combined to form an alkylene group. In this case, the two vicinal lower alkoxy groups form an alkylenedioxy group as a whole. Preferable examples of the alkylenedioxy group include methylenedioxy, ethylenedioxy and propylenedioxy groups.

Examples of substituted wherein R is a halogen atom include fluorine, chlorine, bromine and iodine atoms, with fluorine being preferred.

The hydroxy groups in the 3'- and 5'-positions of 2'-deoxy-5-fluorouridine are esterified with the same fatty acid of the formula $CH_3(CH_2)_nCOOH$ wherein n has the same meanings given above. The number n is preferably 1, 2, 5, 6, 10, 12 and 14. More precisely, preferred residues of fatty acids occupying the 3'- and 5'-positions are propionyl, butanoyl, heptanoyl, octanoyl, dodecanoyl, myristyl and palmitoyl groups.

Preferred compounds of the general formula (I) include:

3-benzoyl-2'-deoxy-3',5'-di-O-butanoyl or -dodecyl-5-fluorouridine, 3-(2,3 or 4-methylbenzoyl)-2'-deoxy-3',5'-di-O-propionyl or -butanoyl-5-fluorouridine, 3-(2,3 or 4-methylbenzoyl)-2'-deoxy-3',5'-di-O-octanoyl or -dodecyl-5-fluorouridine, 3-(2,3- or 3,4-dimethoxybenzoyl)-2'-deoxy-3',5'-propionyl or -butanoyl-5-fluorouridine, 3-(2,3 or 3,4-dimethoxybenzoyl)-2'-deoxy-3',5'-octanoyl or -dodecyl-5-fluorouridine, 3-(2,3- or 4-fluorobenzoyl)-2'-deoxy-3',5'-propionyl or -butanoyl-5-fluorouridine, and 3-(2,3 or 4-fluorobenzoyl)-2'-deoxy-3',5'-myristoyl or -palmitoyl-5-fluorouridine.

In accordance with another embodiment of the present invention, there is provided a process for the preparation of new 2'-deoxy-3',5'-di-O-alkylcarbonyl-5-fluorouridine derivatives of the general formula:

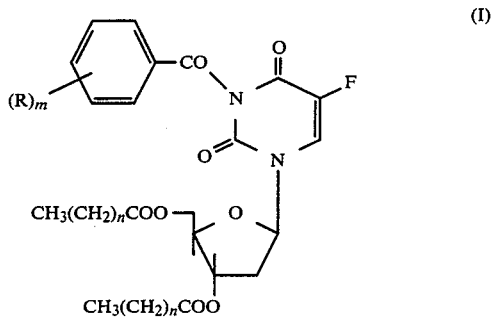

(I)

wherein R stands for an alkyl group, an alkoxy group or a halogen atom, m for zero or an integer of 1–3, and n for an integer of 1–14, with the proviso that when m is 2 or 3, R's may be the same or different and that when m is 2 and the adjacent two R's are alkoxy groups, the two alkyl moieties of the alkoxy groups may be combined to form together with the two adjacent oxa bridging members an alkylenedioxy group as a whole, characterized by reacting a 2'-deoxy-3',5'-di-O-alkylcarbonyl-5-fluorouridine of the general formula:

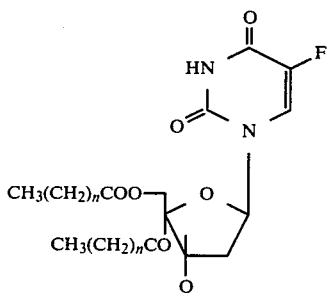 (II)

wherein n has the meaning as given above, with a benzoyl halide of the general formula:

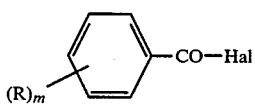 (III)

wherein R and m have the same meanings as given above and Hal for a halogen atom.

In general, 2'-deoxy-3',5'-di-O-alkylcarbonyl-5-fluorouridines of the general formula (II) are known or can easily be prepared by acylating one molar proportion of FUDR with two molar proportion of the corresponding fatty acid preferably in the form of a reactive functional derivative. Benzoyl halides of the general formula (III) are generally known and easily commercially available or can be prepared in a manner known per se. The use of the corresponding chloride or bromide is preferable.

The benzoyl halide of the general formula (III) is preferably used in an amount of 1-3 molar proportion for the 2'-deoxy-3',5'-di-O-alkylcarbonyl-5-fluorouridine of the general formula (II).

The reaction between the benzoyl halide of the general formula (III) and the 2'-deoxy-3',5'-di-O-alkylcarbonyl-5-fluorouridine of the general formula (II), i.e. N-acylation reaction of the fluorouridine with the benzoyl halide, is carried out as a rule in the presence of an organic solvent which is inert to the N-acylation and affords a proper reaction temperature. Illustrative of the preferable organic solvent are aprotic solvents such as diethyl ether, dioxane, chloroform, ethyl acetate, acetonitrile, pyridine, dimethylformamide and dimethylsulfoxide.

The reaction is carried out normally in the presence of an acid-binding agent. The reaction of the present invention is usually promoted by neutralizing a hydrogen halide liberated on the N-acylation of the fluorouridine with the benzoyl halide. Thus, organic bases are generally used as the acid-binding agent. Preferred examples of the organic base include aliphatic tertiary amines such as triethylamine and the like lower trialkylamines and aromatic and heterocyclic tertiary amines such as N,N-dialkylanilines and pyridine which may be substituted by a lower alkyl group or groups. These organic bases are usually miscible with the organic solvent used as the reaction medium but are precipitated when combined with the hydrogen halide. Accordingly, these organic bases can easily be separated from the reaction mixture after completion of the reaction.

The organic base is used usually in an amount of 1-5 moles per mole of the benzoyl halide. As the organic bases per se may be used as the reaction medium, an excess amount of the organic bases, for example, in an amount of 5-20 molar proportion for the benzoyl halide may be used in place of a part or all of the reaction solvent.

The reaction is carried out within a wide range of reaction temperature, for example, under ice cooling or at a temperature up to the boiling point of the reaction solvent used. As a rule, the reaction time is within a period from 30 minutes to 12 hours. It is possible to shorten the reaction time by warming the reaction mixture at the final stage of the reaction.

After completion of the reaction, the end product can be obtained by subjecting the reaction mixture directly to concentration under reduced pressure or by first filtering the reaction mixture and then concentrating the filtrate under the reduced pressure, and finally recrystallizing the resultant residue or subjecting the residue to chromatography on silica gel. If necessary, the last-mentioned purification treatment by the aid of chromatographic operation or recrystallization may be repeated. When the end product is isolated as a viscous oily substance, it can be obtained as a solid or crystalline form by dissolving the oily substance in a small amount of dimethylsulfoxide and pouring the solution into water under vigorous agitation.

The products of the present invention possess high anti-tumor activity with weak toxicity as compared with the known similar FUDR derivatives. The anti-tumor activity and toxicity of the new compounds of this invention were evaluated according to the following tests.

(A) Pharmacological tests for measuring anti-tumor activity:

About 10,000,000 tumor cells of Sarcoma S-180 (successively incubated for several generations in peritoneal cavity of a male mouse of ICR strain) were transplanted subcutaneously into the inguinal region of 5 week-aged male mice of ICR strain. After the lapse of 24 hours, administration of the compounds of this invention started. The administration of the compounds of this invention was forcibly made orally once a day for 7 days. The body weight of each testing animal was measured every day just before the administration. The compounds of this invention were administered dissolved or suspended in polyethylene glycol 400 to each testing animal while polyethylene glycol 400 alone to a control group of the animals. In each case, the same volume of 0.1 ml/10 g (body weight) was administered to each animal. Although the exact doses of the compounds of this invention varied according to the sort of the particular compounds used, the doses were approximately within a range from 0.5 mg/kg to 120 mg/kg. The doses were graded into 3-12 ranks for each testing compound. At each rank, the compound of this invention was administered to a group consisting of 6 mice. As the control group, 18 mice were used.

On the 8th day from the transplantation of the tumor cells each mouse was put to death by bleeding under ether anesthesia. After the tumor tissue was excised, its weight was immediately measured and recorded. An average value of tumor weights in the treated group (referred to as T) for each test compound and for each dose and an average value of tumor weights in the control group (referred to as C) were calculated, respectively, to estimate a dose corresponding to T/C value of 0.70 or 0.50 for each test compound.

Concerning evaluation of the anti-tumor activity, a T/C value within the range of 0.70–0.51 is regarded to be slightly effective, while a value of less than 0.50 is regarded to be effective [Ohyo-Yakuri, 7, 1277–1292 (1973)]. Accordingly, the anti-tumor activity becomes stronger as the value indicating 0.70 or 0.50 in terms of T/C becomes smaller.

(B) Test for measuring toxicity:

Judging from the effects achieved by the compounds of this invention, toxicity values were measured according to the following method, taking accumulative toxicity into consideration.

Groups of 5 weeks old male mice of ICR strain were used for this test, each group consisting of 10 animals. Test compounds were forcibly administered orally once a day for 7 days. The body weight of each animal was measured every day just before the administration. The compounds of this invention were administered in the form dissolved or suspended in polyethylene glycol 400 to each testing animal in the same volume of 0.1 ml/10 g (body weight). Although the exact doses of the compounds of this invention varied according to the sort of the particular compounds used, the doses were approximately within a range from 10 mg/kg to 300 mg/kg. The doses were graded into 5 tanks for each testing compound. At each rank, the compound of this invention was administered to each group. On the 14th day from the completion of administration, the survival and death of the tested animals were judged and $LD_{10}$ values were calculated according to the Litchfield-Wilcoxon method.

The same tests as in the above (A) and (B) were performed, using the following known similar compounds:

A: 2'-Deoxy-3',5'-di-O-n-propionyl-5-fluorouridine
B: 2'-Deoxy-3',5'-di-O-n-butanoyl-5-fluorouridine
C: 2'-Deoxy-3',5'-di-O-n-heptanoyl-5-fluorouridine
D: 2'-Deoxy-3',5'-di-O-n-octanoyl-5-fluorouridine
E: 2'-Deoxy-3',5'-di-O-n-palmitoyl-5-fluorouridine
F: 3-(3,4-methylenedioxybenzoyl)-2'-deoxy-5-fluorouridine
G: 3-(3,4-methylenedioxybenzoyl)-2'-deoxy-3',5'-di-O-acetyl-5-fluorouridine
H: 5-Fluorouracil.

(C) Results of the Tests:

Results of the above Tests (A) and (B) and therapeutic indices calculated therefrom are shown in Table 1. The therapeutic indices were calculated according to the following equation:

Therapeutic index = $LD_{10}$ value ÷ T/C 0.50 value

TABLE 1

| Compound administered | | n | Value indicating T/C 0.70 (mg/Kg) | Value indicating T/C 0.50 (mg/Kg) | $LD_{10}$ (mg/Kg) | Therapeutic index |
|---|---|---|---|---|---|---|
| Compound of the present invention | 2,3-Dimethoxy | 1 | 25 | 44 | 90 | 2.05 |
| | 2,3-Dimethoxy | 14 | 41 | 89 | 130 | 1.46 |
| | H (unsubstituted) | 2 | 23 | 43 | — | — |
| | 3-Methyl | 2 | 8 | 23 | 96 | 4.17 |
| | 2-Methyl | 5 | 4 | 11 | — | — |
| | 2,3-Dimethoxy | 5 | 6 | 18 | 33 | 1.83 |
| | 3-Fluoro | 5 | 1 | 8 | 24 | 3.00 |
| | 2,3-Dimethoxy | 6 | 6 | 20 | 36 | 1.80 |
| | 3-Fluoro | 6 | 7 | 21 | 41 | 1.95 |
| known Compound | A | | 22 | 72 | 108 | 1.50 |
| | B | | 19 | 45 | 70 | 1.55 |
| | C | | 6 | 15 | 24 | 1.60 |
| | D | | 5 | 12 | 19 | 1.58 |
| | E | | 18 | 55 | 71 | 1.29 |
| | F | | 25 | 70 | 61 | 0.87 |
| | G | | 9 | 37 | 43 | 1.16 |
| | H | | 31 | 67 | 63 | 0.94 |

As is evident from the results shown in Table 1, the compounds of the present invention exhibit strong anti-tumor activity at a relatively low level of toxicity, in comparison with the known similar compounds. Thus, the present invention apparently contributes to remarkable improvement in anti-tumor activity and in reduction of toxicity.

According to still another embodiment of the present invention, there is provided anti-tumor agents containing one or more of the new 2'-deoxy-3',5'-di-O-alkylcarbonyl-5-fluorouridine derivatives of the general formula (I) as active ingredients.

In clinical chemotherapy, the compounds of this invention are preferably administered in a daily dose of 1–1000 mg. As a mode of administration, oral administration is preferably applied to the compounds of this invention but parenteral administration such as intravenous injection or intrarectal medication by means of a suppository is also applicable.

As pharmaceutical preparations suitable for oral administration, tablets, capsules (hard capsules and soft capsules), liquids and pills, each unit containing 0.5–500 mg of the compound of this invention as active ingredient, are possible. These preparations may contain, in addition to the active ingredient, other conventional auxiliary components such as milk sugar, corn starch, potato starch, various cane sugar esters of fatty acids, microcrystalline cellulose and polyethylene glycol 4000 as excipients; acacia, gelatine, hydroxypropylcellulose and potato starch as binders; magnesium stearate and talc as lubricants; carboxymethylcellulose calcium, potato starch and corn starch as disintegrating agents. Usual solubilizing agents and suspending agents may also be contained in the preparations, with polyethylene glycol 200–600 being particularly preferred. Examples for a base of suppositories include glycerol, cacao butter, glycerogelatine, polyethylene glycol, laurin and other materials usually employed for this purpose.

Besides the above mentioned additives, materials normally used as carriers for pharmaceutical preparations may also be contained in the anti-tumor agents of the present invention.

The present invention will now be illustrated in more detail by way of examples.

EXAMPLE 1

2.0 Grams of 2'-deoxy-3',5'-di-O-propionyl-5-fluorouridine are dissolved in 25 ml of dry dioxane and the solution is ice cooled. 2 Milliliters of triethylamine and 1.7 g of 2-methylbenzoyl chloride are added to the solution and the mixture is subjected to reaction at room temperature for 15 minutes and then at 70° C. for 30 minutes. The reaction liquid is cooled and triethylamine hydrochloride is filtered off. The filtrate is concentrated under reduced pressure and the oily residue is purified by column chromatography on silica gel (elution solvent: chloroform). The The purified oily substance is dissolved in about 15 ml of dimethyl sulfoxide and the solution is added dropwise to about 400 ml of ice water under vigorous agitation whereupon a precipitate is formed. The resultant precipitate is collected by filtration, washed with water and dried at room temperature under reduced pressure whereby 1.5 g (yield: 56.4%) of powdery 3-(2-methylbenzoyl)-2'-deoxy-3',5'-di-O-propionyl-5-fluorouridine are obtained.

UV-absorption spectrum: $\lambda_{max}^{EtOH}$ 255.5 nm

NMR-spectra: $\delta$(ppm, CDCl$_3$): Uridine moiety: 7.80 (d, H$_6$), 6.19 (broad-t, H$_1$'), near 2.5 (m, H$_2$'), 5.10–5.30 (m, H$_3$'), 4.16–4.42 (m, H$_4$', H$_5$'), 2.10–2.54 (m, 2xCOCH$_2$), 0.98–1.26 (m, 2xCH$_3$). Benzoyl moiety: 7.63 (d, H$_6$), 7.12–7.56 (m, H$_3$, H$_4$, H$_5$), 2.62 (s, CH$_3$).

Elementary analysis (as C$_{23}$H$_{25}$FN$_2$O$_8$): Calc. (%): C 57.98, H 5.29, N 5.88. Found (%): C 57.82, H 5.49, N 5.99.

EXAMPLE 2

2.0 Grams of 2'-deoxy-3',5'-di-O-propionyl-5-fluorouridine are dissolved in 25 ml of dry dioxane and the solution is ice cooled. 2 Milliliters of triethylamine and 1.8 g of 3-fluorobenzoyl chloride are added to the solution and the mixture is subjected to reaction at room temperature for 15 minutes and then at 60° C. for 30 minutes. The reaction liquid is worked up in the same manner as described in Example 1 whereby 2.05 g (yield: 71.5%) of powdery 3-(3-fluorobenzoyl)-2'-deoxy-3', 5'-di-O-propionyl-5-fluorouridine are obtained.

UV-absorption spectra: $\lambda_{max}^{EtOH}$ 251.5 nm.

NMR spectra: $\delta$(ppm, CDCl$_3$):

Uridine moiety: 7.81 (d, H$_6$), 6.18 (broad-t, H$_1$'), near 2.5 (m, H$_2$'), 5.19–5.36 (m, H$_3$'), 4.24–4.48 (m, H$_4$', H$_5$'), 2.20–2.60 (m, 2xCOCH$_2$), 1.05–1.32 (m, 2xCH$_3$). Benzoyl moiety: 7.28–7.76 (m, aromatic H).

Elementary analysis (as C$_{22}$H$_{22}$F$_2$N$_2$O$_8$): Calc. (%): C 55.00, H 4.62, N 5.83. Found (%): C 55.28, H 4.77, N 6.02.

EXAMPLE 3

2.0 Grams of 2'-deoxy-3',5'-di-O-propionyl-5-fluorouridine are dissolved in 25 ml of dry dioxane and the solution is ice cooled. 2 Milliliters of triethylamine and 2.2 g of 2,3-dimethoxybenzoyl chloride are added to the solution and the mixture is subjected to reaction at room temperature for 30 minutes and then at 50° C. for 30 minutes. The reaction liquid is cooled and then triethylamine hydrochloride is filtered off. The filtrate is concentrated under reduced pressure and the residue is purified by column chromatography on silica gel (elution solvent: chloroform). The purified oily substance is allowed to stand overnight at room temperature whereby a part of the substance is crystallized. A small amount of ethanol is added to crystallize the substance wholly and the crystals are collected by filtration whereby 2.3 g (yield: 79.0%) of 3-(2,3-dimethoxybenzoyl)-2'-deoxy-3',5'-di-O-propionyl-5-fluorouridine are obtained. M.P. 84.5°–86° C.

UV-absorption spectra: $\lambda_{max}^{EtOH}$ 264.5, 327 nm.

NMR spectra: $\delta$(ppm, CDCl$_3$): Uridine moiety: 7.72 (d, H$_6$), 6.27 (broad-t, H$_1$'), near 2.5 (m, H$_2$'), 5.16–5.32 (m, H$_3$'), 4.18–4.48 (m, H$_4$', H$_5$'), 2.14–2.48 (m, 2xCOCH$_2$), 1.05–1.32 (m, 2xCH$_3$). Benzoyl moiety: 7.46–7.64 (m, H$_6$), 7.10–7.26 (m, H$_4$, H$_5$), 3.86 (s, OCH$_3$), 3.84 (s, OCH$_3$).

Elementary analysis (as C$_{24}$H$_{27}$FN$_2$O$_{10}$): Calc. (%): C 55.17, H 5.21, N 5.36. Found (%): C 55.27, H 5.37, N 5.50.

EXAMPLE 4

3.0 Grams of 2'-deoxy-3',5'-di-O-myristoyl-5-fluorouridine are dissolved in 20 ml of dry dioxane and the solution is ice cooled. 2.1 Milliliters of triethylamine and 1.4 g of 4-methylbenzoyl chloride are added to the solution and the mixture is subjected to reaction at room temperature for 3 hours. The triethylamine hydrochloride formed is filtered off and the filtrate is concentrated under reduced pressure. The residue is purified by column chromatography on silica gel (elution solvent: chloroform). The resultant purified oily substance is dissolved in ethanol and concentrated under reduced pressure whereupon a crystalline residue is obtained which, after recrystallization from ethanol, gives 1.25 g (yield: 35.4%) of 3-(4-methylbenzoyl)-2'-deoxy-3',5'-di-O-myristoyl-5-fluorouridine. M.P. 76°–77° C.

UV-absorption spectrum: $\lambda_{max}^{EtOH}$ 263 nm.

NMR-spectra: $\delta$(ppm, CDCl$_3$): Uridine moiety: 7.74 (d, H$_6$), 6.26 (broad-t, H$_1$'), near 2.5 (m, H$_2$'), 5.14–5.32 (m, H$_3$'), 4.20–4.44 (m, H$_4$',H$_5$'), 2.20–2.54 (m, 2xCOCH$_2$), 1.04–1.84 (m, 22xCH$_2$), 0.76–1.00 (m, 2xCH$_3$). Benzoyl moiety: 7.78 (d, H$_2$, H$_6$), 7.30 (d, H$_3$, H$_5$), 2.42 (s, CH$_3$).

Elementary analysis (as C$_{45}$H$_{69}$FN$_2$O$_8$): Calc. (%): C 68.85, H 8.86, N 3.57. Found (%): C 68.76, H 8.55, N 3.79.

EXAMPLE 5

3.0 Grams of 2'-deoxy-3',5'-di-O-palmitoyl-5-fluorouridine are dissolved in 25 ml of dry dioxane and the solution is ice cooled. 2 Milliliters of triethylamine and 1.9 g of 2,3-dimethoxybenzoyl chloride are added to the solution and the mixture is subjected to reaction at room temperature for 10 minutes and then at 70° C. for 90 minutes. The reaction liquid is cooled and the precipitated triethylamine hydrochloride is filtered off. The filtrate is concentrated under reduced pressure and the residue is dissolved under heating in ethanol and the solution is allowed to stand whereby crystals are obtained which, after recrystallization from ethanol, affords 2.95 g (yield: 80.2%) of 3-(2,3-dimethoxybenzoyl)-2'-deoxy-3',5'-di-O-palmitoyl-5-fluorouridine. M.P. 77°–78° C.

UV-absorption spectra: $\lambda_{max}^{EtOH}$ 264.5, 327 nm.

NMR-spectra: $\delta$(ppm, CDCl$_3$) Uridine moiety: 7.76 (d, H$_6$), 7.31 (broad-t, H$_1$'), near 2.4 (m, H$_2$'), 5.18–5.34 (m, H$_3$'), 4.22–4.48 (m, H$_4$', H$_5$'), 2.10–2.55 (m, 2xCOCH$_2$), 1.08–1.80 (m, 26xCH$_2$), 0.76–1.06 (m, 2xCH$_3$). Benzoyl moiety: 7.59 (dd, H$_6$), 7.12–7.28 (m, H$_4$, H$_5$), 3.90 (broad-s, 2xOCH$_3$).

Elementary analysis (as C$_{50}$H$_{79}$FN$_2$O$_{10}$): Calc. (%): C 67.69, H 8.98, N 3.16. Found (%): C 68.09, H 9.11, N 2.99.

EXAMPLE 6

3.0 Grams of 2'-deoxy-3',5'-di-O-butanoyl-5-fluorouridine are dissolved in 20 ml of dry dioxane and the solution is ice cooled. 3 Milliliters of triethylamine and 2.0 g of benzoyl chloride are added to the solution and the mixture is subjected to reaction at room temperature for 2 hours. The triethylamine hydrochloride formed is filtered off and the filtrate is concentrated under reduced pressure. The oily residue is purified by column chromatography on silica gel (elution solvent: chloroform) whereby 2.3 g (yield: 60.7%) of 3-benzoyl-2'-deoxy-3',5'-di-O-butanoyl-5-fluorouridine are obtained as an oily substance.

UV-absorption spectrum: $\lambda_{max}^{EtOH}$ 253.5 nm.

NMR-spectra: δ(ppm, CDCl₃): Uridine moiety: 7.76 (d, H₆), 6.27 (broad-t, H₁'), near 2.5 (m, H₂'), 5.15–5.32 (m, H₃'), 4.20–4.46 (m, H₄', H₅'), 2.20–2.52 (m, 2×COCH₂), 1.44–1.92 (m, 2×CH₂), 1.86–1.10 (m, 2×CH₃). Benzoyl moiety: 7.36–8.02 (m, aromatic H).

Elementary analysis (as $C_{24}H_{27}FN_2O_8$): Calc. (%): C 58.77, H 5.55, N 5.71. Found (%) C 58.75, H 5.82, N 5.78.

EXAMPLES 7–23

In the same manner as described in Example 6, a 2'-deoxy-3',5'-di-O-alkylcarbonyl-5-fluorouridine is reacted with an aroyl chloride. Table 5 shows the resulting 2'-deoxy-3',5'-di-O-alkylcarbonyl-5-fluorouridine derivatives and characteristic physical properties thereof.

TABLE 5

| Expl. No. | In General Formula (I) (R)$_m$ n | Yield (%) | Elementary analysis Empirical formula Calc. (%): C, H, N Found (%): C, H, N | UV $\lambda_{max}^{EtOH}$ (nm) | NMR (CDCl₃) δ (ppm) Uridine moiety | NMR (CDCl₃) δ (ppm) Benzoyl moiety |
|---|---|---|---|---|---|---|
| 7 | 3-methyl 2 | 71.6 | C₂₅H₂₉FN₂O₈ 59.52 5.79 5.55 59.59 6.09 5.59 | 257 | 7.75(d,H₆) near 2.4(m,H₂') 4.20–4.44(m,H₄',H₅') 1.44–1.92(m,2×CH₂) 6.26(broad-t,H₁') 5.12–5.32(m,H₃') 2.12–2.56(m,2×COCH₂) 0.84–1.12(m,2×CH₃) | 7.60–7.80(m,H₂,H₆) 7.30–7.52(m,H₄,H₅) 2.40(s,CH₃) |
| 8 | 4-methyl 2 | 71.6 | C₂₅H₂₉FN₂O₈ 59.52 5.79 5.55 59.55 6.82 5.58 | 263.5 | 7.74(d,H₆) near 2.4(m,H₂') 4.22–4.45(m,H₄',H₅') 1.44–1.92(m,2×CH₂) 6.26(broad-t,H₁') 5.15–5.32(m,H₃') 2.16–2.52(m,2×COCH₂) 0.84–1.08(m,2×CH₃) | 7.79(d,H₂,H₆) 7.29(d,H₃,H₅) 2.42(s,CH₃) |
| 9 | 3,4-dimethoxy 2 | 56.2 | C₂₆H—FN₂O₁₀ 56.72 5.68 5.09 56.54 5.60 5.14 | 280.5 315.5 | 7.75(d,H₆) near 2.5(m,H₂') 4.20–4.46(m,H₄',H₅') 1.50–1.90(m,2×CH₂) 6.26(broad-t,H₁') 5.14–5.32(m,H₃') 2.20–2.55(m,2×COCH₂) 0.84–1.10(m,2×CH₃) | 7.55(broad-s,H₂) 7.39(d,H₆) 6.88(d,H₅) 3.91(s,2×OCH₃) |
| 10 | 4-fluoro 2 | 71 | C₂₄H₂₆F₂N₂O₈ 56.69 5.15 5.51 56.74 4.20 5.56 | 255 | 7.78(d,H₆) near 2.5(m,H₂') 4.22–4.48(m,H₄',H₅') 1.46–1.96(m,2×CH₂) 6.27(broad-t, H₁') 5.17–5.34(m,H₃') 2.08–2.60(m,2×COCH₂) 0.84–1.20(m,2×CH₃) | 7.96(dd,H₂,H₆) 7.18(t,H₃,H₅) |
| 11 | 2-methyl 5 | 68.0 | C₃₁H₄₁FN₂O₈ 63.25 7.02 4.76 63.31 7.09 4.79 | 255.5 | 7.78(d,H₆) near 2.4(m,H₂') 4.18–4.44(m,H₄',H₅') 1.08–1.84(m,8×CH₂) 6.27(broad-t,H₁') 5.14–5.32(m,H₃') 2.16–2.52(m,2×COCH₂) 0.72–1.04(m,2×CH₃) | 7.16–7.68(m,aromatic H) 2.68(s,CH₃) |
| 12 | 2,3-dimethoxy 5 | 89.0 | C₃₂H₄₃FN₂O₁₀ 60.56 6.83 4.41 60.60 7.06 4.36 | 265 327 | 7.80(d,H₆) near 2.5(m,H₂') 4.20–4.50(m,H₄',H₅') 1.16–1.88(m,8×CH₂) 6.34(broad-t,H₁') 5.20–5.36(m,H₃') 2.16–2.56(m,2×COCH₂) 0.76–1.08(m,2×CH₃) | 7.56–7.70(m,H₆) 7.18–7.32(m,H₄,H₅) 3.90(s,OCH₃) 3.88(s,OCH₃) |
| 13 | 3-fluoro 5 | 83.6 | C₃₀H₃₈F₂N₂O₈ 60.80 6.46 4.73 60.77 6.48 4.70 | 252 | 7.85(d,H₆) near 2.5(m,H₂') 4.20–4.48(m,H₄',H₅') 1.10–1.84(m,8×CH₂) 6.28(broad-t,H₁') 5.16–5.35(m,H₃') 2.20–2.56(m,2×COCH₂) 0.76–1.06(m,2×CH₃) | 7.28–7.90(m,aromatic H) |
| 14 | 2-methyl 6 | 61.6 | C₃₃H₄₅FN₂O₈ 64.27 7.35 4.54 64.23 7.31 4.59 | 255.5 | 7.80(d,H₆) near 2.5 (m,H₂') 4.22–4.48(m,H₄',H₅') 1.16–1.90(m,10×CH₂) 6.27(broad-t,H₁') 5.16–5.35(m,H₃') 2.18–2.52(m,2×COCH₂) 0.76–1.04(m,2×CH₃) | 7.64(d,H₆) 7.20–7.60(m,H₃,H₄,H₅) 2.68(s,CH₃) |
| 15 | 2,3-dimethoxy 6 | 67.9 | C₃₄H₄₇FN₂O₁₀ 61.62 7.15 4.23 61.69 7.02 4.09 | 265 327 | 7.76(d,H₆) near 2.5(m,H₂') 4.22–4.50(m,H₄',H₅') 1.14–1.96(m,10×CH₂) 6.29(broad-t,H₁') 5.16–5.33(m,H₃') 2.16–2.54(m,2×COCH₂) 0.72–1.04(m,2×CH₃) | 7.58(dd,H₆) 7.14–7.30(m,H₄H₅) 3.87(s,OCH₃) 3.85(s,OCH₃) |
| 16 | 3-fluoro 6 | 84.0 | C₃₂H₄₂F₂N₂O₈ 61.92 6.82 4.51 61.73 6.72 4.40 | 251.5 | 7.86(d,H₆) near 2.5(m,H₂') 4.26–4.50(m,H₄',H₅') 1.14–2.00(m,10×CH₂) 6.30(broad-t,H₁') 5.20–5.36(m,H₃') 2.22–2.58(m,2×COCH₂) 0.74–1.06(m,2×CH₃) | 7.24–7.92(m,aromatic H) |
| 17 | hydrogen 10 | 66.9 | C₄₀H₅₉FN₂O₈ 67.20 8.32 3.92 67.16 8.30 4.00 | 253 | 7.80(d,H₆) near 2.5(m,H₂') 4.20–4.54(m,H₄',H₅') 1.20–2.00(m,18×CH₂) 6.28(broad-t,H₁') 5.16–5.35(m,H₃') 2.20–2.60(m,2×COCH₂) 0.76–1.08(m,2×CH₃) | 7.40–8.10(m,aromatic H) |
| 18 | 3-methyl 10 | 54.9 | C₄₁H₆₁FN₂O₈ 67.56 8.44 3.84 67.59 8.41 3.81 | 257.5 | 7.79(d,H₆) near 2.5(m,H₂') 4.20–4.48(m,H₄',H₅') 1.10–2.00(m,18×CH₂) 6.29(broad-t,H₁') 5.16–5.36(m,H₃') 2.15–2.60(m,2×COCH₂) 0.70–1.10(m,2×CH₃) | 7.30–8.00(m,aromatic H) 2.38(s,CH₃) |
| 19 | 2,4-dimethoxy 10 | 34 | C₄₂H₆₃FN₂O₁₀ 65.09 8.19 3.61 65.25 8.65 3.79 | 278 304 | 7.63(d,H₆) near 2.5(m,H₂') 4.16–4.44(m,H₄',H₅') 1.04–1.80(m,18×CH₂) 6.26(broad-t,H₁') 5.10–5.30(m,H₃') 2.20–2.50(m,2×COCH₂) 0.78–1.04(m,2×CH₃) | 8.01(d,H₆) 6.57(dd,H₅) 6.36(d,H₃) 3.83(s,OCH₃) 3.74(s,OCH₃) |
| 20 | hydrogen 12 | 43.2 | C₄₄H₆₇FN₂O₈ 68.54 8.76 3.63 68.36 8.75 3.87 | 253 | 7.60(d,H₆) near 2.4(m,H₂') 4.05–4.35(m,H₄',H₅') 1.00–1.80(m,22×CH₂) 6.07(broad-t,H₁') 5.00–5.16(m,H₃') 2.05–2.50(m,2×COCH₂) 0.70–1.00(m,2×CH₃) | 7.10–7.85(m,aromatic H) |
| 21 | 2-fluoro | 42.3 | C₄₄H₆₆F₂N₂O₈ | 250 | 7.62(d,H₆) | 6.06(broad-t,H₁') | 6.80–7.92(m,aromatic H) |

TABLE 5-continued

| Expl. No. | In General Formula (I) (R)$_m$ n | Yield (%) | Elementary analysis Empirical formula Calc. (%): C, H, N Found (%): C, H, N | UV $\lambda_{max}^{EtOH}$ (nm) | NMR (CDCl$_3$) δ (ppm) Uridine moiety | | Benzoyl moiety |
|---|---|---|---|---|---|---|---|
| | 12 | | 66.98 8.43 3.55 66.89 8.32 3.81 | | near 2.4(m,H$_2'$) 4.04–4.44(m,H$_4'$,H$_5'$) 0.96–1.80(m,22×CH$_2$) | 5.00–5.20(m,H$_3'$) 2.04–2.48 (m,2×COCH$_2$) 0.72–0.98(m,2×CH$_3$) | |
| 22 | 2-methyl 14 | 39.2 | C$_{49}$H$_{77}$FN$_2$O$_8$ 69.97 9.23 3.33 69.89 8.84 3.29 | 254.5 | 7.71(d,H$_6$) near 2.4(m,H$_2'$) 4.10–4.40(m,H$_4'$,H$_5'$) 1.00–2.00(m,26×CH$_2$) | 6.16(broad-t,H$_1'$) 5.06–5.24(m,H$_3'$) 2.15–2.45(m,2×COCH$_2$) 0.75–1.00(m,2×CH$_3$) | 7.54(d,H$_6$) 7.07–7.46(m,H$_3$,H$_4$,H$_5$) 2.62(s,CH$_3$) |
| 23 | 3-fluoro 14 | 79.8 | C$_{48}$H$_{74}$F$_2$N$_2$O$_8$ 68.22 8.83 3.31 68.17 8.53 3.35 | 252 | 7.74(d,H$_6$) near 2.4(m,H$_2'$) 4.20–4.44(m,H$_4'$,H$_5'$) 1.12–1.80(m,26×CH$_2$) | 6.21(broad-t,H$_1'$) 5.10–5.28(m,H$_3'$) 2.16–2.44(m,2×COCH$_2$) 0.76–1.02(m,2×CH$_3$) | 7.20–7.76(m,aromatic H) |

The preparation of the anti-tumor agents of the present invention will now be illustrated in more detail by way of the following typical preparation examples:

(A) Hard capsule preparations

| Recipe: | |
|---|---|
| 3-(2,3-dimethoxybenzoyl-2'-deoxy-3',5'-di-O—n-propionyl-5-fluorouridine | 80 mg |
| aliphatic acid ester of sucrose | 20 mg |
| milk sugar | 165 mg |
| crystallinecellulose | 24 mg |
| hydroxypropylcellulose of a low degree of substitution | 8 mg |
| magnesium stearate | 3 mg |
| total | 300 mg |

Capsules (No. 2) are formed according to a conventional method so that each capsule may contain the above dose of ingredients. In general 3–9 capsules per day can be administered orally to adult patients.

(B) Soft capsule preparations

| Recipe: | |
|---|---|
| 3-(3-fluorobenzoyl-2'-deoxy-3',5'-di-O—n-palmitoyl-5-fluorouridine | 50 mg |
| polyethylene glycol 400 | 250 mg |
| propylene glycol | 10 mg |
| bleached beeswax | 10 mg |
| total | 320 mg |

Capsules are formed according to a conventional method so that each capsule may contain the above dose of ingredients. As a rule, 3–9 capsules per day can be administered orally to adult patients.

It is understood that the preceding representative examples may be varied within the scope of the present specification both as to reactants and reaction conditions, by those skilled in the art to achieve essentially the same results.

As many widely different embodiments of this invention may be made without departing from the spirit and scope thereof, it is construed that the present invention is not limited to the specific embodiments thereof except as defined in the appended claims.

What is claimed is:

1. 2'-Deoxy-3',5'-di-O-alkylcarbonyl-5-fluorouridine derivatives of the general formula:

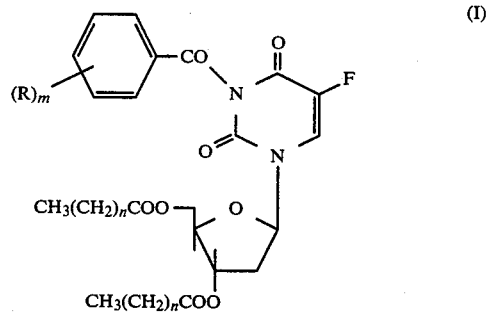

wherein R stands for an alkyl group, an alkoxy group or a halogen atom, m for zero or an integer of 1–3, and n for an integer of 1–2 or 5–14, with the proviso that when m is 2 or 3, R's may be the same or different and that when m is 2 and the adjacent two R's are alkoxy groups, the two alkyl moieties of the alkoxy groups may be combined to form together with the two adjacent oxa bridging members an alkylenedioxy group as a whole.

2. 2'-Deoxy-3',5'-di-O-alkylcarbonyl-5-fluorouridine derivatives according to claim 1, wherein m in the general formula (1) stands for zero.

3. 2'-Deoxy-3',5'-di-O-alkylcarbonyl-5-fluorouridine derivatives according to claim 1, wherein R in the general formula (1) stands for methyl group.

4. 2'-Deoxy-3',5'-di-O-alkylcarbonyl-5-fluorouridine derivatives according to claim 1, wherein R in the general formula (1) stands for methoxy group and m is 2.

5. 2'-Deoxy-3',5'-di-O-alkylcarbonyl-5-fluorouridine derivatives according to claim 1, wherein R in the general formula (1) stands for fluorine atom.

6. 2'-Deoxy-3',5'-di-O-alkylcarbonyl-5-fluorouridine derivatives according to claim 1, wherein n is 2.

7. 2'-Deoxy-3',5'-di-O-alkylcarbonyl-5-fluorouridine derivatives according to claim 1, wherein n is 1.

8. 2'-Deoxy-3',5'-di-O-alkylcarbonyl-5-fluorouridine derivatives according to claim 1, wherein n is 5.

9. A pharmaceutical composition comprising an effective anti-tumor amount of at least one 2'-deoxy-3',5'-di-O-alkylcarbonyl-5-fluorouridine derivative of the general formula:

$$(I)$$

[Structure: benzene ring with $(R)_m$ substituent, connected via $-CO-$ to N of a uracil ring bearing F at 5-position; N1 connected to a deoxyribose sugar with $CH_3(CH_2)_nCOO-$ groups at 3' and 5' positions]

wherein R stands for an alkyl group, an alkoxy group or a halogen atom, m for zero or an integer of 1–3, and n for an integer of 1–2 or 5–14, with the proviso that when m is 2 or 3, R's may be the same or different and that when m is 2 and the adjacent two R's are alkoxy groups, the two alkyl moieties of the alkoxy groups may be combined to form together with the two adjacent oxa bridging members an alkylenedioxy groups as a whole and a pharmaceutically acceptable carrier or excipient.

10. A pharmaceutical composition as in claim 9, wherein R in the general formula (I) stands for methyl group and n is 2.

11. A pharmaceutical composition as in claim 9, wherein R in the general formula (I) stands for methoxy group, m is 2 and n is 1.

12. A pharmaceutical composition as in claim 9, wherein R in the general formula (I) stands for fluorine atom and n is 5.

13. A pharmaceutical composition as in claim 9, wherein R is methyl, m is 1 and n is 2.

14. A pharmaceutical composition as in claim 9, wherein the carrier is polyethylene glycol and cane sugar esters of fatty acids.

15. A pharmaceutical composition as in claim 9, wherein R is methoxy, m is 2 and n is 14.

16. A pharmaceutical composition as in claim 9, wherein m is zero and n is 2.

17. A pharmaceutical composition as in claim 9, wherein R is methyl, m is 1 and n is 5.

18. A pharmaceutical composition as in claim 9, wherein R is methoxy, m is 2 and n is 5.

19. A pharmaceutical composition as in claim 9, wherein R is methoxy, m is 2 and n is 6.

20. A pharmaceutical composition as in claim 9, wherein R is fluorine, m is 1 and n is 6.

21. A method for treating tumors comprising administering an effective anti-tumor amount of at least one 2'-deoxy-3',5'-di-O-alkylcarbonyl-5-fluorouridine derivative of the general formula:

$$(I)$$

[Structure: same as above]

wherein R stands for an alkyl group, an alkoxy group or a halogen atom, m for zero or an integer of 1–3, and n for an integer of 1–2 or 5–14, with the proviso that when m is 2 or 3, R's may be the same or different and that when m is 2 and the adjacent two R's are alkoxy groups, the two alkyl moieties of the alkoxy groups may be combined to form together with the two adjacent oxa bridging members an alkylenedioxy group as a whole.

22. A method for treating tumors as in claim 21, wherein R is methyl and n is 2.

23. A method for treating tumors as in claim 21, wherein R is methoxy, m is 2 and n is 1.

24. A method for treating tumors as in claim 21, wherein R is fluorine and n is 5.

25. A method for treating tumors as in claim 21, wherein R is methyl, m is 1 and n is 2.

26. A method for treating tumors as in claim 21, wherein R is methoxy, m is 2 and n is 14.

27. A method for treating tumors as in claim 21, wherein m is zero and n is 2.

28. A method for treating tumors as in claim 21, wherein R is methyl, m is 1 and n is 5.

29. A method for treating tumors as in claim 21, wherein R is methoxy, m is 2 and n is 5.

30. A method for treating tumors as in claim 21, wherein R is methoxy, m is 2 and n is 6.

31. A method for treating tumors as in claim 21, wherein R is fluorine, m is 1 and n is 6.

* * * * *